United States Patent [19]

Scott

[11] Patent Number: 4,604,280
[45] Date of Patent: * Aug. 5, 1986

[54] STABILIZATION OF CARRAGEENAN-CONTAINING TOOTHPASTE

[75] Inventor: George V. Scott, Scotch Plains, N.J.

[73] Assignee: Colgate-Palmolive Co., New York, N.Y.

[*] Notice: The portion of the term of this patent subsequent to Oct. 12, 1999 has been disclaimed.

[21] Appl. No.: 648,557

[22] Filed: Sep. 10, 1984

Related U.S. Application Data

[63] Continuation of Ser. No. 406,610, Aug. 6, 1982, Pat. No. 4,473,988, which is a continuation of Ser. No. 87,561, Oct. 24, 1979, Pat. No. 4,353,890.

[51] Int. Cl.$^4$ .................. A61K 7/16; A61K 41/00; A61L 2/12; B01J 1/10
[52] U.S. Cl. ................ 424/49; 204/157.68; 219/10.55 B; 219/20; 252/315.3
[58] Field of Search .................. 424/49–58, 424/361; 53/440; 219/10.55 M

[56] References Cited

U.S. PATENT DOCUMENTS

| | | | |
|---|---|---|---|
| 3,469,996 | 9/1969 | Endres et al. | 99/118 |
| 3,535,482 | 10/1970 | Kluck | 219/10.55 |
| 3,711,604 | 1/1973 | Colodney et al. | 424/52 |
| 3,840,657 | 10/1974 | Norfleet | 424/49 |
| 3,963,892 | 6/1976 | Camph et al. | 219/10.55 M |
| 4,003,554 | 1/1977 | Chauffoureaux | 259/4 AC |
| 4,353,890 | 10/1982 | Scott | 424/49 |
| 4,457,908 | 7/1984 | Scott | 424/49 |
| 4,473,988 | 10/1984 | Scott | 53/440 |
| 4,474,818 | 10/1984 | Scott | 424/358 |

OTHER PUBLICATIONS

Pages 339–341 of Cosmetics, Science and Technology, by Sagarin.
Microwave Power in Industry, edited by W. A. G. Voss and W. R. Tinga, Second Edition, published Jan. 1978.
Industrial Applications of Microwave Energy, edited by R. B. Smith, published in 1976.

Primary Examiner—Shep K. Rose
Attorney, Agent, or Firm—R. L. Stone; M. M. Grill; H. S. Sylvester

[57] ABSTRACT

A method for stabilizing a cosmetic composition containing carrageenan, specifically, a toothpaste, wherein microwave radiation, preferably in the 0.8 to 3 gigahertz frequency range, is directed onto the toothpaste so as to raise its temperature to at least the gel-sol transition temperature of the carrageenan, after which the toothpaste is quiescently cooled to room temperature. The use of microwave radiation facilitates an even heating of the toothpaste, so that temperature sensitive components thereof are not adversely affected, and promotes excellent control of temperature regulation. Heating of the dentifrice, with improved thickening and stabilization thereof, is obtainable by passing it through a conduit while directing microwave radiation onto it and then filling it into suitable dispensing containers, or by filling the dentifrice into such containers and then subjecting them to microwave radiation.

4 Claims, 4 Drawing Figures

STABILIZATION OF CARRAGEENAN-CONTAINING TOOTHPASTE

This is a continuation of application Ser. No. 406,610, filed Aug. 6, 1982, now U.S. Pat. No. 4,473,988, issued Oct. 2, 1984, which is a continuation of Ser. No. 087,651, field 10/24/79, now U.S. Pat. No. 4,353,890.

This invention relates to the stabilization of cosmetic compostions. More particularly, it relates to stabilizing toothpastes that contain carrageenan as a gelling agent.

Carrageenan is a known constituent of various cosmetic and dentifrice formulations. It is a useful gelling agent and thickener for cosmetics generally and is especially useful for thickening toothpastes and for helping to hold in suspension therein the dispersed particulate solid polishing agent in a liquid or semi-solid medium. Although carrageenan is a satisfactory stabilizer it has been noted that the viscosity or thickness of compositions in which it is a gelling agent tends to decrease when such compositions are subjected to mechanical working. Even relatively minor working, such as that experienced when the toothpaste is pumped or otherwise conveyed at room temperature, can cause substantial decreases in viscosities. To allow for this and still obtain a product of desired thickness, it has often been necessary to employ additional amounts of carrageenan beyond those which would be sufficient without any such viscosity decrease.

Viscosity decreases can be avoided to a significant extent by avoiding working the dentifrice when its temperature is below the gel-sol transition point of carrageenan but in conventional plants for the manufacture of toothpastes this may often be impracticable or difficult because there may often be delays between times when a dentifrice formulation is manufactured and when it is ready for filling into dispensing containers. Thus, the dentifrice will often be cooled and will have to be pumped, conveyed or otherwise worked, before filling is to be effected.

Although heating of a carrageenan-containing composition, such as a toothpaste incorporating carrageenan as a gelling agent, can increase the viscosity of the subsequently cooled toothpaste, in normal dentifrice manufacturing installations open mixing heaters and other conventional heating apparatuses will be unsatisfactory, because they may cause losses of moisture and volatile flavor components, changes in flavor compositions and changes in other dentifrice constituents, due to local overheating and aeration of the paste. Additionally, production time is lost due to the usually slow heating that is effected to avoid harm to the product. Also, further undesirable mechanical working results because pumping of the toothpaste out of the heating means is usually required. The present invention, which utilizes microwave heating to raise the temperature of a carrageenan-containing toothpaste to at least the gel-sol transition temperature of the carrageenan, thereby overcomes various serious objections to temperature modification of dentifrices to improve stabilities thereof.

Patent and literature searches made for the present inventor have not disclosed or suggested the use of microwave radiation for heating a carrageenan-containing toothpaste to improve the stability and increase the viscosity thereof. Of the patents and publications found in such searches, it is considered that the most relevant are: U.S. Pat. Nos. 3,469,996; 3,535,482; 3,963,892; and 4,003,554. U.S. Pat. No. 3,469,996 describes the tempering of a monoglyceride shortening product by subjecting it to microwave radiation. U.S. Pat. No. 3,535,482 relates to rapid microwave heating of fluids, as for pasturization, sterilization and concentration thereof. U.S. Pat. No. 3,963,892 illustrates the microwave heating of flowing blood, controlled to prevent overheating. Finally, U.S. Pat. No. 4,003,554 describes the employment of microwave radiation to induce a phase change in a polar polymer during malaxating thereof. Although the references cited relate to various means of applying microwave radiation to materials to affect their properties, although it is well known to utilize microwave radiation for heating a wide variety of substances, and although carrageenan is a known gelling agent for dentifrices, various properties of which have been recognized in the art, none of the references describes the present invention and none suggests it or the exceedingly beneficial results thereof. In accordance with the present invention a method for stabilizing a cosmetic composition containing carrageenan comprises directing microwave radiation onto such composition in such quantity as to raise the temperature thereof to at least the gel-sol transition temperature of the carrageenan, and quiescently cooling the composition to room temperature. Also within the invention are methods for increasing the viscosities of carrageenan-containing toothpastes by microwave radiation treatment of the toothpaste compositions before or after packing into dispensing containers. In some cases such treatment is effected after packing into cartons and boxes and in other instances both treatments prior to and after such packing are carried out. Also within the invention are temperature controlling methods of heating dentifrices with microwaves, recirculating methods of heating, and intermittent heatings, and an apparatus adapted for ready installation into filling lines so as to effect such microwave heating when desired.

The invention will be readily understood by reference to the accompanying description, taken in conjunction with the drawing, in which.

Figure 1:
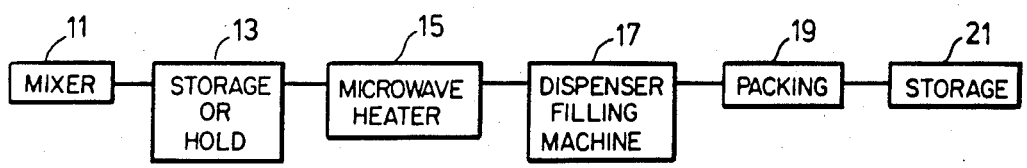
FIG. 1 is a schematic representation of steps in the manufacture of a carrageenan-containing cosmetic, such as a toothpaste, from mixing to storage.

In FIG. 1 mixer 11 represents a means for compounding various components of a cosmetic, e.g., a dentifrice, and blending them to desired final product form. The dentifrice of this invention includes carrageenan as a gelling agent. While the dentifrice may be made at room temperature, it is usually desirable, at least for gelling of the carrageenan components, for the temperature of at least a part of the composition to be raised above the gel-sol point of the carrageenan. Homogenizers and other processing equipment are considered as being represented by mixer 11. After mixing of the dentifrice, with or without prior cooling, it may be filled directly into dispensing packages, but in FIG. 1, usually due to production exigencies, there is shown a storage or hold 13, during which the temperature of the mixer will usually be below the gel-sol transition point. In the usual manufacturing process the dentifrice is moved from storage to the filling machine, normally by pump or conveyer means, which has an adverse effect on the gel and diminishes product viscosity or thickness. Therefore, by the method of the present invention, after the storage or hold step 13, the product is heated in microwave heater means 15 long enough to raise the temperature thereof above the gel-sol transition temperature, after which dispensing containers are filled in machine 17, the containers are cartoned and packed at 19, and are sent to storage, represented by numeral 21. The products stored, after testing, are found to have appreciably greater viscosities than control products treated similarly but not subjected to microwave heating. Due to the short period of microwave heating, the enclosed nature of the heating and the minimum of mechanical disruption at a temperature below the gel-sol transition temperature, to which the dentifrice is taken, deterioration of its flavoring materials is not noted and high viscosities of product are obtained.

Figure 2:
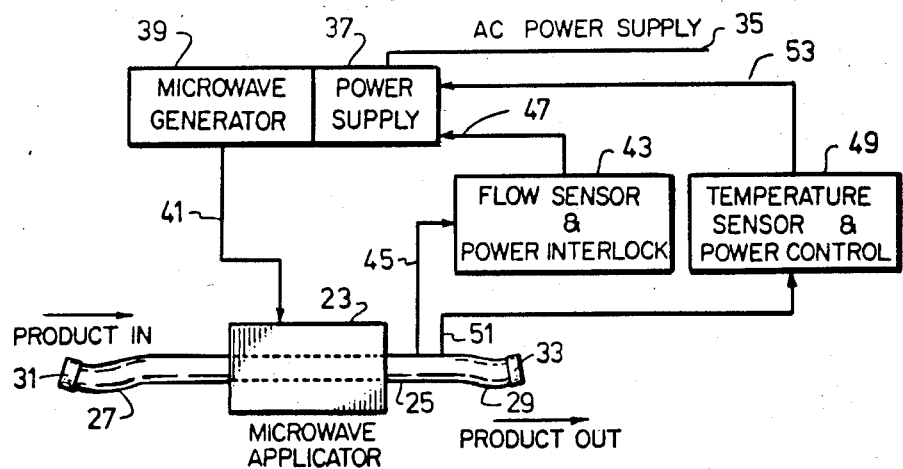
FIG. 2 is a schematic diagram of an installation of a microwave applicator in a conveying line for a dentifrice.

In FIG. 2 microwave applicator 23 is illustrated enclosing a microwave-transparent walled conduit 25, having flexible end portions 27 and 29 and fastening means 31 and 33 thereon, for fastening onto portions of a conveyer, conduit, pipe or tube arrangement, not shown, in a standard dentifrice filling line. An alternating current power supply line 35 conveys electricity to the power supply 37 for a microwave generator 39, which generates microwave energy and transmits it to the microwave applicator through means represented by line 41. The installation illustrated is self-controlling, with the microwave generator being turned off when product is not flowing through line 25 and with the flow of microwave energy being regulated (such regulation can be by means of on-off operations or by control of power to the generator) in response to the temperature of the material in such tube. Flow sensor 43 has a probe portion 45 connected to conduit 25 where such conduit emerges from the microwave applicator, and the sensor acts to cut off electrical flow to the power supply 37, via a contact represented by numeral 47, when the sensor indicates no flow of material is occurring. Temperature sensor 49, with a probe connection slightly downstream of the flow sensor on conduit 25, which probe is represented by numeral 51, transmits via line 53 a signal which controls the power supply to the generator and applicator, increasing such supply (or turning it on) when the product temperature is lower than desirable (when product flows).

Figure 3:
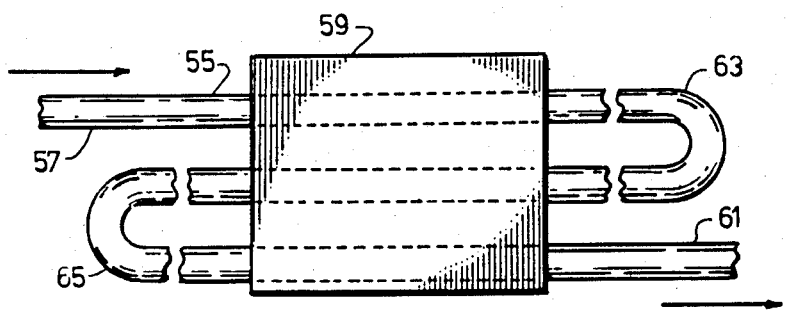
FIG. 3 is a schematic plan view of a portion of a variation of the apparatus of FIG. 2.
Figure 4:
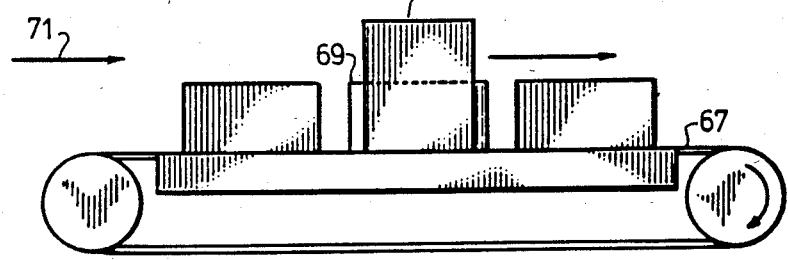
FIG. 4 is an elevational view of a conveyer with a microwave applicator associated with it, suitable for heating packaged dentifrice.

In FIG. 3 conduit 55 is shown to be of S-shape, with inlet portion 57 transporting contents through microwave applicator 59, out of the applicator, back into it, out of it and back through it to exit through outlet line portion 61. Thus, the dentifrice or other carrageenan-containing cosmetic passes through the microwave applicator three (or more) times, with the periods in which it is outside the applicator, as at 63 and 65, being "consolidation" periods when the heat generated in the material is transferred through it without imposition of additional heat, so as to facilitate evening out of the heating effect. Of course, the system control shown in FIG. 2 may also be applied to the variation of the invention in this figure, as may be the processing shown in FIG. 1. In FIG. 4 there is represented conveyer 67, supporting and moving a case 69 of cartons of filled dispensing dentifrice containers, which cases, cartons and containers are of microwave-transparent material. As illustrated, case 69 is moving in the direction of arrow 71 through microwave applicator 73, which heats the contents of the dispensing containers in the cartons and cases. Interlocks and temperature controls of types resembling those of FIG. 2 may be adapted for installation on the embodiment of the invention illustrated in this figure.

Although the present invention is most relevant to improving the stability and thickness of toothpastes, the teachings hereof are also applicable to the preparation of carrageenan-thickened and -stabilized other cosmetic materials, such as gel and paste shampoos, hand cleaners, skin fresheners, skin cleaners and perfumes. Also, related types of compositions, such as salves and ointments, thickened liquid soaps and detergents and various other preparations in which carrageenan or mixtures of carrageenan and other gums or thickeners are employed to stabilize and/or thicken the products, may be improved. Hereinafter specific reference will be to toothpastes, which are often more difficult to stabilize and thicken satisfactorily, due to their contents of soluble particulate materials and possibly to the more stringent standards applied to such products because they are employed orally.

The illustrations following are specific to dentifrice compositions but many of the components utilized in dentifrices are also useful in various other cosmetic and similar compositions, among which components are solvents or vehicles, surface active agents or detergents, thickeners or gelling agents, polishing agents, emollients, buffering agents, flavors and perfumes.

Dentifrice compositions, such as toothpastes, normally comprise a vehicle, a polishing agent, a gelling agent and a surface active agent or a detersive material. The usual vehicles of dentifrices are water and lower polyhydric alcohols of 3 to 6 hydroxyl groups and 3 to 6 carbon atoms per molecule. The most preferred humectant vehicles are glycerol and sorbitol, usually in an aqueous medium. Often it will be most preferable to employ glycerol-sorbitol mixtures. When transparent dentifrices, often referred to as gel dentifrices, are manufactured, the index of refraction of vehicle used will be approximately the same as that of the polishing agent and the proportion of moisture in the product will often be held to a minimum. Instead of glycerol and sorbitol, other liquid polyols may also be utilized, such as polyethylene glycols, mannitols, other sugar alcohols and polyoxyethylene alcohols.

Dentifrice polishing agents are usually finely divided water insoluble powdered materials of particle sizes such that they pass a 140 mesh screen, U.S. Standard Sieve series, and preferably are from 1 to 40 microns in diameter, more preferably being 2 to 20 microns in diameter, with particle size distributions being normal over such ranges. Examples of suitable inorganic water insoluble powdered materials are dicalcium phosphate, tricalcium phosphate, insoluble sodium metaphosphate, crystalline silica, colloidal silica, complex aluminosilicates, aluminum hydroxide (including alumina trihydrate), magnesium phosphate, magnesium carbonate, calcium carbonate, calcium pyrophosphate, bentonite, talc, calcium silicate, calcium aluminate, aluminum oxide, aluminum silicate and silica xerogels, all of which have polishing activity but are not objectionably abrasive.

The synthetic organic detergents or surface active agents which may be employed in the present compositions assist in emulsifying or otherwise dispersing the components of the dentifrice uniformly and add their cleaning action to the product. In some cases they are germicidal and aid in prophylaxis. Although the organic surface active materials used may be anionic, nonionic, ampholytic or cationic, it is generally preferred to employ, at least as a major detersive constituent, either an anionic or nonionic material or mixture thereof. Of the anionics and cationics the anionics are usually found superior in most compositions and a reason for such superiority is their desirable foaming action, in addition to their excellent cleaning ability. Generally, the anionic detergents will include long chain hydrophobic fatty or poly-lower alkoxy groups plus hydrophilic groups. These detergents will normally be in the form of salts, especially water soluble salts of alkali metals. Among the anionic detergents that are useful may be named the higher fatty acid monoglyceride sulfates, the higher alkyl sulfates, higher linear alkyl aryl sulfonates, higher olefin sulfonates, higher alkyl sulfoacetates, higher aliphatic acyl amides of lower aliphatic aminocarboxylic acid compounds, higher alkyl poly-lower alkoxy (of 3 to 100 alkoxy groups) sulfates and higher fatty acid soaps. Normally the higher alkyl groups will be 10 to 18 or 12 to 16 carbon atoms, as will be the higher olefins, the aliphatic groups will be alkyls, preferably normal alkyls, and the aromatic groups will be benzene. Examples of such materials include sodium hydrogenated coconut oil fatty acids monoglyceride monosulfate, sodium lauryl sulfate, sodium linear tridecylbenzene sulfonate, sodium N-lauroyl sarcoside and sodium cocate. Among the nonionic detergents are those including chains of lower alkylene oxides, e.g., ethylene oxide, propylene oxide, in which ethylene oxide chains make up the hydrophilic portions. Exemplary of such materials are the Pluronics ®, Igepals ®, Ucons ®, Neodols ® and Tergitols ®. The higher fatty alcohol polyethylene oxide condensation products of 10 to 18 carbon atoms in the alcohol and 3 to 15 ethoxy groups per mol are preferred, e.g., Neodol 25-7, Neodol 45-11. Additional detergents are recited in the text *Surface Active Agents*, Vol. II (1958), by Schwartz, Perry and Berch.

In addition to the four main types of constituents of dentifrices, the gelling agent of which still is to be discussed, it is recognized that there are present in many dentifrices various other materials, including flavorings, enamel hardening agents, antibacterial compounds, astringent compounds, protein precipitating agents and effervescent mixtures. Of these, among the most important are the flavoring materials, which, in addition to sweetening agents, such as saccharin, include essential oils, aldehydes, esters, alcohols and similar materials known in the art. Exemplary of the essential oils are spearmint, peppermint, wintergreen, sassafras, clove, sage, eucalyptus, lemon and lime. Among the enamel hardening agents may be mentioned sodium monofluorophosphate, sodium fluoride and stannous fluoride. Some of the dentifrice components and adjuvants may deteriorate or react with others if the temperature is raised too high, even locally, and even small percentages of decomposition may give rise to definite taste differences, which would make the consumer critical of the product. Accordingly, it is important to avoid such deteriorations.

The gelling agents that may be employed in manufacturing various dentifrice compositions may be selected from a wide variety of available materials, some natural, some synthetic and some hybrid. Of these, it has been found that carrageenan, an excellent gelling agent otherwise, has the undesirable property of exhibiting a lowering of viscosity when gels thereof are mechanically worked, sometimes only comparatively slightly, at a temperature below the gel-sol temperature, which, in the case of carrageenan, is in the range of about 45° to 49° C., more narrowly 46° to 48° C. Although carrageenan is an excellent gelling agent, producing very satisfactory dentifrice gels at reasonable concentrations, because of this viscosity decrease more carrageenan is required to ensure that a worked product will be of sufficient thickness or viscosity for end use and even if a sufficient quantity of carrageenan is employed it is possible that the end products from differently worked batches will be of different thicknesses, depending on the treatments they have been given (which treatments may be different). The characteristics exhibited by carrageenan have not been found to be typical of other gelling agents but it has been noted that when carrageenan is mixed with other such agents, for example, with sodium carboxymethyl cellulose, treatment by the method of the present invention results in significantly improved viscosity of the dentifrice product, providing that the proportion of carrageenan is at least 20% of the gelling agent present. Instead of sodium carboxymethyl cellulose there may be substituted, in mixture with carrageenan, other dentifrice gelling agents such as hydroxyethylcarboxyethyl cellulose, polyvinyl pyrrolidone, gum tragacanth, hydroxypropylmethyl cellulose, methyl cellulose, starch, starch glycolate, polyvinyl alcohol, sodium alginate, carob bean gum and hydrophilic colloidal hydroxyvinyl polymers, such as Carbopols ®, to name only a few. Of course, the present invention is also applicable to stabilizing viscosities of toothpastes and other cosmetic products thickened by gums or gelling agents exhibiting viscosity improvement upon heating, like carageenan.

Research in connection with the present invention has related mostly to the utilization of commercial carrageenans, such as mixtures of the sodium salts of lambda and kappa carrageenans. However, it is considered that the present invention applies also to various other carrageenan salts, such as the calcium, potassium, and sodium salts of lambda, kappa and and iota carrageenans, as well, and to various mixtures of them. Also, mixtures of kappa carrageenan and locust bean gum are often of improved gelling powers and are suitable for application of the present invention. Preferably, because the kappa carrageenan produces a gel, whereas the lambda carrageenan does not gel, but thickens instead, for the firmest gels a major proportion of the carrageenan present will often be of the kappa type or of iota or mixed kappa and iota. However, since the kappa carrageenan gels most strongly with potassium ions and the iota carrageenan gels most strongly with calcium ions, when potassium ions are present one may wish to use the kappa carrageenan and when calcium ions are present in the system it may be desirable to utilize more of the iota form of the carrageenan. Normally, the toothpaste or other cosmetic medium will be at a neutral or alkaline pH, or will be near neutrality, if it is acidic. Acidic pH's, and especially strongly acidic pH's, tend to hydrolyze carrageenan solutions, although when they are in the gelled state they are generally considered to be stable if in the kappa or iota form (the lambda hydrolyzes and does not gel). The molecular weight of the carrageenans will normally be in the range of 5,000 to about 500,000, with most of those commercially employed being in the range of about 100,000 to 500,000. Preferably, such molecular weights will be in the range of 225,000 to 275,000. The gel-sol transition temperatures for the carrageenans vary depending on the particular carrageenan or carrageenan mixture and the composition of the medium in which it is present. Thus, for 1% of kappa carrageenan in water, the gelling temperature can be raised from about 5° C. to as high as 60° C. by increasing the potassium ion contact from 0 to about 1%. Similarly, with respect to iota carrageenan, an increase in the calcium ion content from 0 to 1% may increase the gelling temperature from about 44° C. to 72° C. The gelling of kappa carrageenan is usually effected by heating to a temperature of about 70° C. or more, followed by cooling, with a firm gel usually being formed at a temperature between 45° and 65° C., which remelts when the temperature is raised 10° to 20° C. above the setting temperature. When lambda carrageenan is mixed with kappa carrageenan, as in the preferred gelling agents of the present invention, it has been found that in the dentifrice compositions described the gel-sol point may be in the range of 45° to 49°. If, technically, this temperature does not result in gel-sol transition, nevertheless, an improvement in viscosity or thickness of the product is obtainable by heating it to such a temperature, or higher. A preferred carrageenan mixture is that sold under the name Viscarin ® GMC but it is also considered that other commercial products, such as Gelcarin ® HWG, SeaGel ® GH, Gelcarin DG, Gelcarin SI, SeaKem ® 5, Seaspen ® PF, Seaspen IN, Gelcarin LMR, Gelcarin MMR, Gelcarin HMR, Gelcarin MAC, Gelcarin MIF, SeaKem C, SeaKem D, SeaKem 9 and SeaKem FL 2 will also be applicable. Such products are available from the Marine Colloids Division of FMC Corporation and descriptions of them are found in Monograph No. 1 of Marine Colloids, Inc. and a Technical Bulletin entitled Technical Seminar Notes, published by Marine Colloids Division of FMC Corporation, Springfield, N.J. 07081.

In the present toothpastes the proportion of carrageenan utilized will usually be in the range of 0.1 to 5% weight. When the carrageenan is only one of several types of thickeners or gelling agents present, the proportion thereof, for useful stabilization effects to be obtained by the present invention, will be at least 20% of the total of gelling agent in the toothpaste and usually the total of gelling agent then present will be no more than 5% of the toothpaste, by weight. Normally when carrageenan is the thickener (but also when it is only a part of the thickener but the previous conditions are satisfied) the toothpaste will comprise from about 10 to 70 or 75% of particulate polishing agent, 0.2 to 3% of carrageenan, 0.2 to 20% of foaming agent, 2 to 50% of polyhydric alcohol and 5 to 50% of water. With such components there may also be present various adjuvants, in a proportion up to no more than 20%, ususally no more than 10% and preferably less than 5% of the toothpaste. In some preparations it is possible to eliminate the polyhydric alcohol entirely and in some water content may be minimized by either water or polyhydric alcohol and preferably a mixture of both will be present as the vehicle. Also, for good microwave heating some lossy dielectric material, such as water or other polar and highly dielectric substance should be present. For the purpose of the present invention water is a highly desirable component of the product and often is essential.

For aqueous toothpaste systems the preferred proportions of components are from 40 to 60% of polishing agent, 0.5 to 2% of carrageenan (or thickener mixture), 0.2 to 10% of foaming agent or detergent, 5 to 35% of polyhydric alcohol and 8 to 30% of water, with more preferable proportions being 45 to 55%, 0.5 to 1.5%, 0.5 to 5%, 15 to 30% and 20 to 30%, respectively. For gel dentifrices these proportions may be 10 to 50%, 0.5 to 2%, 5 to 15%, 30 to 75% and 10 to 30%. Adjuvant content for both opaque and clear toothpastes and gels will preferably be in the range of 0.5 to 5%, with flavoring preferably being from 0.5 to 2.5% thereof. When chloroform is present, as a flavoring means or purge assistant, as is permitted in some circumstances, it may constitute an additional 1 to 5% of the product. Any other adjuvants present will usually not exceed 5% of the product, total. Methods for the manufacture of suitable dentifrices of this invention are described in various patents, included among which are U.S. Pat. Nos. 3,711,604 and 3,840,657, in which the dentifrice is degassed or has bubbles intentionally added to it, in both of which cases the method of this invention is additionally advantageous.

Microwave generators and applicators are familiar processing apparatuses and need not be described at length herein. Although the microwave spectrum may be considered to extend from about 0.3 to 300 gigahertz, with the corresponding wave lengths being from one meter to one millimeter, microwave radiation will usually be in the range of 0.3 to 50 gigahertz, and as a practical matter, in the United States, will be within the range of 0.8 to 3 gigahertz because of the uses of the 0.915 and 2.45 gigahertz bands (in Great Britain the 0.896 gigahertz band is employed). Various industrial applications of microwave technology have been described in publications of The International Microwave Power Institute (Canada), including *Microwave Power in Industry*, edited by W. A. G. Voss and W. R. Tinga, Second Edition, published January, 1978, and *Industrial Applications of Microwave Energy*, edited by R. B. Smith, published in 1976. As is related in these reference publications, microwave radiation, whether generated by klystron or magnetron (most of those relating to the present invention are magnetron apparatuses) has been used in a variety of industrial applications for heating, polymerizing, drying, gelatinizing and otherwise radiation-affecting various materials. However, there is no description or suggestion of the method of the present invention or the advantages thereof in such publications.

The amount of microwave energy to be transmitted to a toothpaste in accordance with the present invention is not considered to be critical providing that the temperature of the toothpaste is raised sufficiently so as to improve the room temperature thickness or viscosity of the product after cooling. Thus, it is considered that to obtain desirable thickening and stabilizing results one should raise the temperature above the gel-sol transition temperature of the carrageenan under the conditions prevailing, but so long as the desired viscosity increasing effect is obtained the treatment is useful. Rates of feed, times of microwave radiation application, throughputs of toothpaste, etc., may be readily calculated from the power of the microwave generator and the specific heat of the product being treated. Thus, one kilowatt hour equals about 860 kilocalories or about 3,420 British thermal units, so that a kilowatt equals about 14.3 kilocalories per minute or about 57 BTU per minute. The efficiency of a magnetron microwave applicator, which may be taken as about 50 to 60%, should also be calculated in to determine the power of the magnetron unit required to obtain desirable throughputs. The size of the microwave applicator to be installed in a given operation will usually be determined by various circumstances, such as space available, desired throughput rate, material treated, etc., but usually will be such as to heat the toothpaste to the desired temperature in a relatively short time, less than five minutes for bulk treatments and no more than two minutes for in-line treatments. Preferably, the microwave exposure is limited to one minute, more preferably, 30 seconds and most preferably, 15 seconds.

The following examples illustrate but do not limit the invention. Unless otherwise indicated all parts are by weight and all temperatures are in °C.

EXAMPLES

| | Percent |
|---|---|
| Glycerol | 4.5 |
| Sorbitol | 17.5 |
| Viscarin GMC (kappa-lambda carrageenan, mf'd. by FMC Corporation) | 1.0 |
| Sodium benzoate | 0.5 |
| Sodium saccharin | 0.2 |
| Water | 22.4 |
| Dicalcium phosphate (90% hydrate) | 45.3 |
| Fumed Silica (Cab-O-Sil ® M5) | 5.0 |
| Sodium lauryl sulfate | 1.5 |
| Sodium fluoride | 0.5 |
| Sodium monofluorophosphate | 1.0 |
| Peppermint flavor | 0.6 |
| | 100.0 |

The above opaque toothpaste formula is obtained by mixing the components in known manner in a conventional mixer, at room temperature, after initially dispersing the carrageenan in glycerol, and subsequently, in water at an elevated temperature, preferably about 70° C. However, the final mix temperature is about 37° C., with 30 minutes of mixing being employed and with degassing being effected during a later part of the total mix time, using vacuum means drawing 700 millimeters of mercury, after which the toothpaste is transferred to storage overnight. From storage, the toothpaste is mechanically conveyed to an automatic filling apparatus, by which it is filled into toothpaste tubes. Subsequently, after two days storage, the contents of such tubes are tested for the consistency thereof. The tests employed include Brookfield-Helipath viscosity measurements and thickness measurements as described below. Viscosity is measured by employing a suitable spindle of the Brookfield viscosimeter, testing a number of samples of the toothpaste at a temperature of about 27° C. and averaging the results. Comparatively, synthetic organic polymeric dispensing containers, having body portions of polyethylene and caps of polypropylene, are filled with the dentifrice, sealed and subjected to microwave heating for fifteen seconds each, to allow the absorption of sufficient microwave energy to raise the temperature of the contents from about 27° C. to temperatures in the range of about 57° C. to 71° C., and are allowed to cool quiescently to about 27° C. After two days of standing the dentifrices in such tubes are measured for consistency. In the consistency test a "Cuban" tester is used to supplement and confirm the Brookfield-Helipath viscosity readings. Such viscosity measurements are made with a Brookfield viscosimeter Model RVF, at four r.p.m., with Helipath and TF spindle. In the confirmatory "Cuban" test the dentifrice is squeezed from a tube through a fixed size orifice across a grid of parallel rods, increasingly spaced apart. The test results are expressed as the greatest space number (numbers are from 1 through 12), which represents the longest distance between rods that support the dentifrice ribbon without having it break. It has been found that Brookfield readings and Cuban tester readings are substantially directly related. The comparative testing shows that, using a large number of samples, viscosity readings for the untreated product are increased substantially by the microwave treatment effected, with viscosity gains, in centipoises, almost always being more than 50% and often being almost 90%, with an average increase of about 73%. The results reported are also obtained when the dentifrices are microwave heated as described but in glass tubes. Similar results are obtained when microwave treatment is effected in the microwave applicator schematically illustrated in FIG. 2, with the toothpaste treated being one that has been degassed in a batch mixer, having a vacuum connection, has stood overnight, has then been microwave treated while being conveyed to the automatic filling machine, and after filling, has been allowed to cool quiescently. In such operation, when filling is effected with the toothpaste still warm and preferably above the gel-sol transition temperature, such filling may be speeded, due to the lower viscosity of the heated toothpaste (although it increases in viscosity upon cooling, compared to a control).

In variations of the above described experiments the application of microwave radiant energy to toothpaste being pumped through a line passing within a microwave applicator may be multipass and in some instances the line may have internal guides to promote mixing during heating. As shown in FIG. 3, when utilizing multipass heating, the dentifrice may be removed from the microwave chamber periodically so as to promote additionally improved heat distribution (the microwave heater already gives good heat distribution, compared to various other heating means). The product, made by utilizing the apparatus of FIG. 3, after filling into dentifrice tubes and cooling quietly, will be increased in viscosity and thickness, like those products previously described.

In another variation of the invention, after filling of the toothpaste into microwave-transparent dispensing containers, such as those made of polyethylene and polypropylene, and capping (with polypropylene caps) or otherwise sealing, then, either before or after the dispensing containers are packed in cartons and cases, such product may be subjected to microwave radiation in such quantity as is calculated to heat it to the desired temperature in the 45°–75° C. range, preferably 46° to 60° C. or 46° to 48° C. range, after which it is cooled without mechanical working. The case and carton materials are essentially transparent to microwave radiation, as are the polymeric plastic components of the dispensing tubes, so the toothpaste is the only material appreciably heated. The toothpaste in such tubes is also of greater viscosity and consistency than control paste not so microwave treated.

In other variations of the invention the apparatus illustrated in FIG. 2 is installed in a filling line for the filling of the described carrageenan-stabilizer toothpaste and, with the flow sensor and temperature sensor operating as described previously, automatically heats the toothpaste to 48° C. and above the gel-sol transition temperature of the carrageenan in that environment, so that the filled toothpaste is of improved and increased room temperature viscosity and thickness. Of course, the toothpaste is not subjected to significant mechanical working after cooling appreciably and preferably is delivered still warm to the filling head. After completion of the particular run the apparatus is readily changed to another filling line, also running a carrageenan-thickened toothpaste formula, and such composition is similarly microwave treated.

The various products described do not exhibit any objectionable loss of flavor and show no evidence of any decomposition of constituents greater than in the various controls. By utilizing the apparatus and methods mentioned it is possible to improve the quality control ratings for product viscosity and to make such viscosities in final commercial products closer to desired standards. Also, in those instances when excess carrageenan had previously been employed as a thickener and stabilizer, the proportion thereof can be decreased, up to as much as 50%, while still obtaining a product of acceptable thickness.

The present invention is also applicable to compositions containing carrageenan and other supplementing thickeners, such as sodium carboxymethyl cellulose. When, for example, in the above formula, half of the carrageenan is replaced by sodium carboxymethyl cellulose, and the same treatments are effected, although the gain in viscosity is not as great, it is still appreciable, being about 23%. However, when cellulosic gums are used instead of carrageenan, and no carrageenan is present, the gains are not noteworthy.

This invention is applicable to various other dentifrice formulas than those previously given in this example. For examples, when, instead of the gums and thickening agents shown therein, carrageenan is used in the same or equivalent proportions to effect similar thickenings in Formulas 1–15, appearing at pages 339–341 of *Cosmetics: Science and Technology*, by Sagarin, herein incorporated by reference, and the toothpastes resulting are microwave heated as described, similar desirable thickening and consistency improving results are obtainable. Furthermore, when transparent gel dentifrices, thickened with carrageenan or partly thickened with carrageenan gelling agents, such as Viscarin GMC, are microwave treated in the manner described, improved viscosities and consistencies also result. Similar results are not obtained when cellulosic gums replace the carrageenans and are not obtained when, after microwave heating, the dentifrices are subjected to mechanical workings or agitations at temperatures below the gel-sol transition temperature.

The preceding examples have illustrated operations of the present invention and various advantages thereof. It will be evident from them and the accompanying description that the present invention allows one to increase and control the viscosity, consistency, form retention and thickness of flowable cosmetic products, such as toothpastes, containing carrageenan as a gelling agent. The invention also allows one to reduce the level of carrageenan employed to obtain a desirable viscosity in the final product.

While it is possible to improve the viscosity of the cosmetic products by processing them at elevated temperature and maintaining this temperature until the products are filled, such is usually not practicable for dentifrices, due to normal production interruptions, eight-hour working days rather than around-the-clock production, shutdowns and changeovers. Also, a considerable loss of volatile materials, such as moisture and flavor, could take place if the product were kept hot during storage. Reheating in the storage tank is generally unsatisfactory because air is introduced during such mixing and volatiles are lost. Continuous heating of conduits for the toothpaste by electrical, steam or other means is relatively slow, inefficient and non-uniform, and it can scorch the product. All such disadvantages are overcome by the present invention and, in addition, because of the product being thinned due to microwave treatment, pumping is effected at lower power consumption, better mixing is obtained and filling and transfer steps can be effected easier and quicker.

When compared to conventional heating methods, microwave heating, with its instantaneous on-off switching and selective power control, allows instant response to detected conditions. Thus, when the toothpaste is no longer moving through the conduit at the microwave applicator, as in the example given, the power is shut off immediately, and when the temperature rises above the desired limit, such shutoff or reduction in power occurs. There is no lag in response. All the power delivered is converted to heat in the toothpaste, with essentially none being lost. Only the paste is heated, not the oven walls, conduits, etc. (except by conduction). The microwave radiation unit does not heat the work space surrounding the unit. The microwave equipment is clean, quiet and readily susceptible to temperature, rate of heat transfer, viscosity and flow sensing controls. Such sensors prevent overheating or underheating of the product. The heating of the product is internal and uniform and such uniformity may be further increased (although it is not considered as needed), by stirring the microwave field or by mechanically moving the product within the conduit as it passes before the microwaves. The heating rate may be increased by the application of more power, by changing the time the product is subjected to the microwaves and by recycling material. An advantage of the present method is that as the temperature increases, the toothpaste, and most high moisture natural cosmetic products, heat faster by microwave radiation, which speeds heating further. The system is preferably a closed system, so that as the product passes before the microwave radiation there are no aeration or evaporation and no flavor losses caused by evaporation.

The various advantages described are so significant that extensive tests of the present method have been made to verify initial laboratory results. Toothpastes containing carrageenan gelling agent were obtained from commercial productions in a number of countries and were tested to determine whether the viscosity thereof could be improved by the present method. Thirteen different toothpastes, prepared under a variety of manufacturing and filling conditions, and from different formulations, were tested, and the viscosity increases ranged from 46 to 89%, averaging 69%. For another set of samples, from nine different countries, the average viscosity gain was 62%, with only one sample being below 40%. Samples from commercial production, which included a 50:50 carrageenan:cellulose gum thickening agent, resulted in an averge gain of 42% in viscosity (for eleven samples). Accordingly, plants installing the present invention are expected to produce thicker toothpastes or to be able to decrease the amount of carrageenan or carrageenan-other gum mixture employed, while still obtaining desired thickness and maintaining quality control standards. In such installations the microwave unit should be installed between the toothpaste storage tank and the final filling units so that the finished dentifrice may be heated before filling, and even if severely mechanically worked before filling, the dentifrice will have improved consistency at room temperature. Alternatively, the filled plastic tubes of dentifrice can be microwave heated, as previously described. However, even if the dentifrice is heated and then stored overnight, so as to be returned to room temperature before filling, an improvement in viscosity is obtained.

Laboratory experiments have indicated that about one kilowatt-minute per kilogram is required to heat a toothpaste to a temperature 25° C. above its initial temperature. Depending on power cost, this works out to be less than 0.1¢ per normal five-ounce tube of toothpaste and such costs may be recovered by savings in gelling agent consumed. Thus, use of a 20 kw. microwave unit allows the production of 1,200 kilograms/hr. or approximately 7,500 tubes/hr. of heated toothpaste.

In additional experiments it has been found that repetitive microwave treatments do not appreciably increase product viscosity (beyond about 5%) and that product viscosity does not appear to depend on the cooling rate after exposure of the product to microwaves. Storage tests on treated products show that after lengthy storage, up to six months, the toothpaste viscosities are still consistently higher than those of untreated product, although there is some normal decrease in viscosity on storage for treated and untreated products.

The invention has been described with respect to various illustrations and embodiments thereof but is not to be limited to these because it is evident that one of skill in the art, with the present specification before him, will be able to utilize substitutes and equivalents without departing from the invention.

What is claimed is:

1. A process for stabilizing a cosmetic composition containing carrageenan as a gelling agent, which comprises directing microwave radiation onto such composition in such quantity as to raise the temperature thereof to at least the gel-sol transition temperature of the carrageenan, and quiescently cooling the dentifrice from such gel-sol transition temperature to produce gelation thereof.

2. A process according to claim 1 wherein the cosmetic composition is a toothpaste in which carrageenan is present in a gelling proportion from about 0.1 to 5% by weight, the quiescent cooling of the toothpaste is from the gel-sol transition temperature of the carrageenan to room temperature, and the toothpaste viscosity is increased by the process due to gelation of the carrageenan.

3. A method according to claim 2 wherein the carrageenan is at least 20% of the gelling agent in the toothpaste, the total of gelling agent is no more than 5% of the weight of the toothpaste and the microwave radiation is at a frequency in the range of 0.8 to 3 gigahertz.

4. A method according to claim 2 wherein the toothpaste comprises from about 10 to 70% of particulate polishing agent, 0.2 to 3% of carrageenan, 0.2 to 20% of foaming agent, 2 to 50% of polyhydric alcohol and 5 to 50% of water, the polishing agent, carrageenan, foaming agent, polyhydric alcohol and water are mixed together before microwave heating of the toothpaste and such heating is to a temperature of at least 46° C.

* * * * *